United States Patent [19]

Hirai et al.

[11] 4,141,901
[45] Feb. 27, 1979

[54] PROCESS FOR PRODUCING TRIAZOLYLBENZOPHENONE DERIVATIVES

[75] Inventors: Kentato Hirai, Kyoto; Toshio Fujishita, Nishinomiya; Teruyuki Ishiba, Takatsuki; Hiroshiko Sugimoto, Ikeda, all of Japan

[73] Assignee: Shionogi & Co., Ltd., Osaka, Japan

[21] Appl. No.: 861,010

[22] Filed: Dec. 15, 1977

Related U.S. Application Data

[60] Division of Ser. No. 722,670, Sep. 13, 1976, abandoned, which is a continuation of Ser. No. 718,934, Aug. 30, 1976, abandoned.

[30] Foreign Application Priority Data

Dec. 30, 1975 [GB] United Kingdom ............... 53224/75

[51] Int. Cl.$^2$ ............................................. C07D 249/14
[52] U.S. Cl. .................................. 260/308 R; 424/269
[58] Field of Search ............................. 260/308 R Primary Examiner—Jose Tovar
Attorney, Agent, or Firm—Wenderoth, Lind & Ponack

[57] ABSTRACT

Triazolylbenzophenone derivatives of the formula:

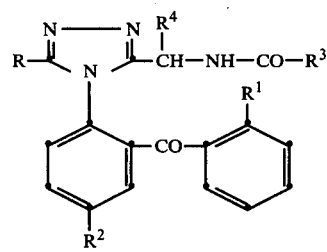

(wherein R represents hydrogen, $C_1$–$C_6$ alkyl, $C_1$–$C_6$ halo-alkyl, the group $-(CH_2)_n$-X-$R^5$, or the group

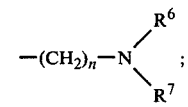

$R^5$ represents hydrogen, $C_1$–$C_6$ alkyl, $C_2$–$C_6$ alkenyl, $C_2$–$C_6$ alkynyl, $C_6$–$C_{10}$ aryl, or $C_2$–$C_8$ acyl; X represents sulfur or oxygen; n represents 0, 1, 2, or 3; $R^6$ and $R^7$ each represents hydrogen or $C_1$–$C_6$alkyl; or the group

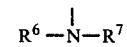

represents pyrrolidino, piperidino, morpholino, or γ-methylpiperazino; $R^1$ represents hydrogen or halogen; $R^2$ represents halogen nitro, or trifluoromethyl; $R^3$ represents $C_1$–$C_6$ alkyl, $C_1$–$C_6$ halo-alkyl, $C_1$–$C_6$ azido-alkyl, $C_6$–$C_{10}$ aryl, $C_2$–$C_8$ acyl, or the group

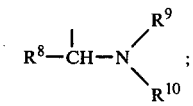

$R^4$ and $R^8$ each represents hydrogen, $C_1$–$C_6$ alkyl, or $C_7$–$C_{10}$ aralkyl; $R^9$ represents hydrogen or $C_1$–$C_6$ alkyl; $R^{10}$ represents hydrogen, $C_1$–$C_6$ alkyl, $C_7$–$C_{10}$ aralkyl, or $C_2$–$C_{11}$ α-amino-acyl; or the group

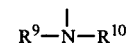

represents phthalimido, pyrrolidino, piperidino, morpholino, or γ-methylpiperazino) and their pharmaceutically acceptable acid addition salts, useful as anxiolytics, sedatives, hypnotics, anticonvulsants, muscle relaxants, antidepressants, their synthetic intermediates, and their preparation.

1 Claim, No Drawings

PROCESS FOR PRODUCING TRIAZOLYLBENZOPHENONE DERIVATIVES

This is a division of Ser. No. 722,670, filed Sept. 13, 1976, now abandoned, which is a continuing application of Ser. No. 718,934, filed Aug. 30, 1976, now abandoned.

The present invention relates to triazolylbenzophenone derivatives of the formula:

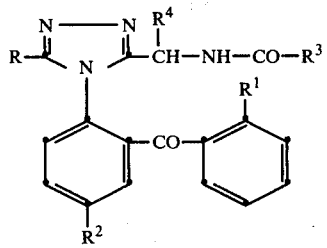

(wherein R represents hydrogen, $C_1$–$C_6$ alkyl, $C_1$–$C_6$ halo-alkyl, the group —$(CH_2)_n$—X—$R^5$, or the group

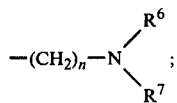

$R^5$ represents hydrogen, $C_1$–$C_6$ alkyl, $C_2$–$C_6$ alkenyl, $C_2$–$C_6$ alkynyl, $C_6$–$C_{10}$ aryl, or $C_2$–$C_8$ acyl; X represents sulfur or oxygen; n represents 0, 1, 2, or 3; $R^6$ and $R^7$ each represents hydrogen or $C_1$–$C_6$ alkyl; or the group

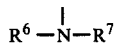

represents pyrrolidino, piperidino, morpholino, or γ-methylpiperazino; $R^1$ represents hydrogen or halogen; $R^2$ represents halogen, nitro, or trifluoromethyl; $R^3$ represents $C_1$–$C_6$ alkyl, $C_1$–$C_6$ halo-alkyl, $C_1$–$C_6$ azido-alkyl, $C_6$–$C_{10}$ aryl, $C_2$–$C_8$ acyl, or the group

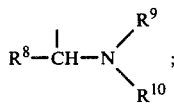

$R^4$ and $R^8$ each represents hydrogen, $C_1$–$C_6$ alkyl, or $C_7$–$C_{10}$ aralkyl; $R^9$ represents hydrogen or $C_1$—$C_6$ alkyl; $R^{10}$ represents hydrogen, $C_1$–$C_6$ alkyl, $C_7$–$C_{10}$ aralkyl, or $C_2$–$C_{11}$ α-amino-acyl; or the group

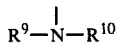

represents phthalimido, pyrrolidino, piperidino, morpholino, or γ-methylpiperazino) and their pharmaceutically acceptable acid addition salts, which are useful as anxiolytics, sedatives, hypnotics, anticonvulsants, muscle relaxants, antidepressants, as well as their synthetic intermediates.

The above groups are exemplified as follows: alkyl (e.g. methyl, ethyl, isopropyl, butyl, pentyl, hexyl), alkenyl (e.g. vinyl, allyl, butenyl, pentenyl, hexenyl), alkynyl (e.g. ethynyl, propynyl, butynyl, pentynyl), aryl (e.g. phenyl, tolyl, xylyl, pyridyl), aralkyl (e.g. benzyl, phenethyl, phenylpropyl), acyl (e.g. formyl, acetyl, propionyl, benzoyl, carbobenzoxy), α-amino-acyl (e.g. glycyl, alanyl, leucyl, phenylalanyl), and halogen (e.g. chlorine, bromine, fluorine, iodine).

Specific examples of the triazolylbenzophenone derivatives (I) are:

2′,5-dichloro-2-(3-acetamidomethyl-5-methyl-4H-1,2,4-triazol-4-yl)-benzophenone;

2′,5-dichloro-2-(3-propionamidomethyl-5-methyl-4H-1,2,4-triazol-4-yl)-benzophenone;

2′,5-dichloro-2-(3-isobutyramidomethyl-5-methyl-4H-1,2,4-triazol-4-yl)-benzophenone;

2′,5-dichloro-2-(3-butyramidomethyl-5-methyl-4H-1,2,4-triazol-4-yl)-benzophenone;

2′,5-dichloro-2-(3-pyruvamidomethyl-5-methyl-4H-1,2,4-triazol-4-yl)-benzophenone;

2′,5-dichloro-2-(3-L-phenylalanylaminomethyl-5-methyl-4H-1,2,4-triazol-4-yl)-benzophenone;

5-chloro-2-(3-glycylaminomethyl-5-dimethylaminomethyl-4H-1,2,4-triazol-4-yl)-benzophenone;

5-chloro-2-(3-glycylaminomethyl-5-morpholinomethyl-4H-1,2,4-triazol-4-yl)-benzophenone;

5-chloro-2-(3-glycylaminomethyl-5-piperidinomethyl-4H-1,2,4-triazol-4-yl)-benzophenone;

5-chloro-2-[3-(4-methoxybenzamidomethyl)-5-dimethylaminomethyl-4H-1,2,4-triazol-4-yl]-benzophenone;

5-chloro-2-(3-butyramidomethyl-5-dimethylaminomethyl-4H-1,2,4-triazol-4-yl)-benzophenone;

5-chloro-2-(3-acetamidomethyl-5-dimethylaminomethyl-4H-1,2,4-triazol-4-yl)-benzophenone;

2′,5-dichloro-2-(3-glycylaminomethyl-5-dimethylaminomethyl-4H-1,2,4-triazol-4-yl)-benzophenone;

2′,5-dichloro-2-(3-glycylaminomethyl-5-diethylaminomethyl-4H-1,2,4-triazol-4-yl)-benzophenone;

2′,5-dichloro-2-(3-glycylaminomethyl-5-pyrrolidinomethyl-4H-1,2,4-triazol-4-yl)-benzophenone;

2′,5-dichloro-2-(3-glycylaminomethyl-5-phenylthiomethyl-4H-1,2,4-triazol-4-yl)-benzophenone;

2′,5-dichloro-2-(3-glycylaminomethyl-5-propylthiomethyl-4H-1,2,4-triazol-4-yl)-benzophenone;

2′,5-dichloro-2-[3-(2-diethylaminoacetamidomethyl)-5-diethylaminomethyl-4H-1,2,4-triazol-4-yl]-benzophenone;

2′,5-dichloro-2-[3-(2-γ-methylpiperazino-acetamidomethyl)-5-γ-methylpiperazinomethyl-4H-1,2,4-triazol-4-yl]-benzophenone;

2′,5-dichloro-2-[3-(N^α-glycyl-glycylaminomethyl)-5-methyl-4H-1,2,4-triazol-4-yl]-benzophenone;

2′,5-dichloro-2-[3-(N^α-L-phenylalanyl-glycylaminomethyl)-5-methyl-4H-1,2,4-triazol-4-yl]-benzophenone;

5-chloro-2-(3-glycylaminomethyl-5-acetoxymethyl-4H-1,2,4-triazol-4-yl)-benzophenone;

5-chloro-2-(3-glycylaminomethyl-5-pyrrolidinomethyl-4H-1,2,4-triazol-4-yl)-benzophenone;

2′,5-dichloro-2-(3-glycylaminomethyl-5-methyl-4H-1,2,4-triazol-4-yl)-benzophenone;

5-chloro-2-(3-glycylaminomethyl-4H-1,2,4-triazol-4-yl)-benzophenone;

5-chloro-2-(3-glycylaminomethyl-5-methyl-4H-1,2,4-triazol-4yl)-benzophenone;

5-chloro-2-[3-(2-chloroacetamidomethyl)-5-methyl-4H-1,2,4-triazol-4-yl]-benzophenone;

5-chloro-2-[3-(2-dimethylaminoacetamidomethyl)-5-methyl-4H-1,2,4-triazol-4-yl]-benzophenone;

5-chloro-2-[3-(2-methylaminoacetamidomethyl)-5-methyl-4H-1,2,4-triazol-4-yl]-benzophenone;

5-chloro-2-[3-(2-diethylaminoacetamidomethyl)-5-methyl-4H-1,2,4-triazol-4-yl]-benzophenone;

2',5-dichloro-2-[3-(2-chloroacetamidomethyl)-5-methyl-4H-1,2,4-triazol-4-yl]-benzophenone;

2',5-dichloro-2-[3-(2-dimethylaminoacetamidomethyl)-5-methyl-4H-1,2,4-triazol-4-yl]-benzophenone;

2',5-dichloro-2-[3-(2-diethylaminoacetamidomethyl)-5-methyl-4H-1,2,4-triazol-4-yl]-benzophenone;

5-chloro-2-(3-glycylaminomethyl-5-propargyloxymethyl-4H-1,2,4-triazol-4-yl)-benzophenone;

5-chloro-2'-fluoro-2-(3-glycylaminomethyl-5-morpholinomethyl-4H-1,2,4-triazol-4-yl)-benzophenone; and 5-chloro-2-(3-L-phenylalanylaminomethyl-5-methyl-4H-1,2,4-triazol-4-yl)-benzophenone.

The triazolylbenzophenone derivatives (I) can be prepared through three routes (Routes A, B, and C) as shown in the following scheme:

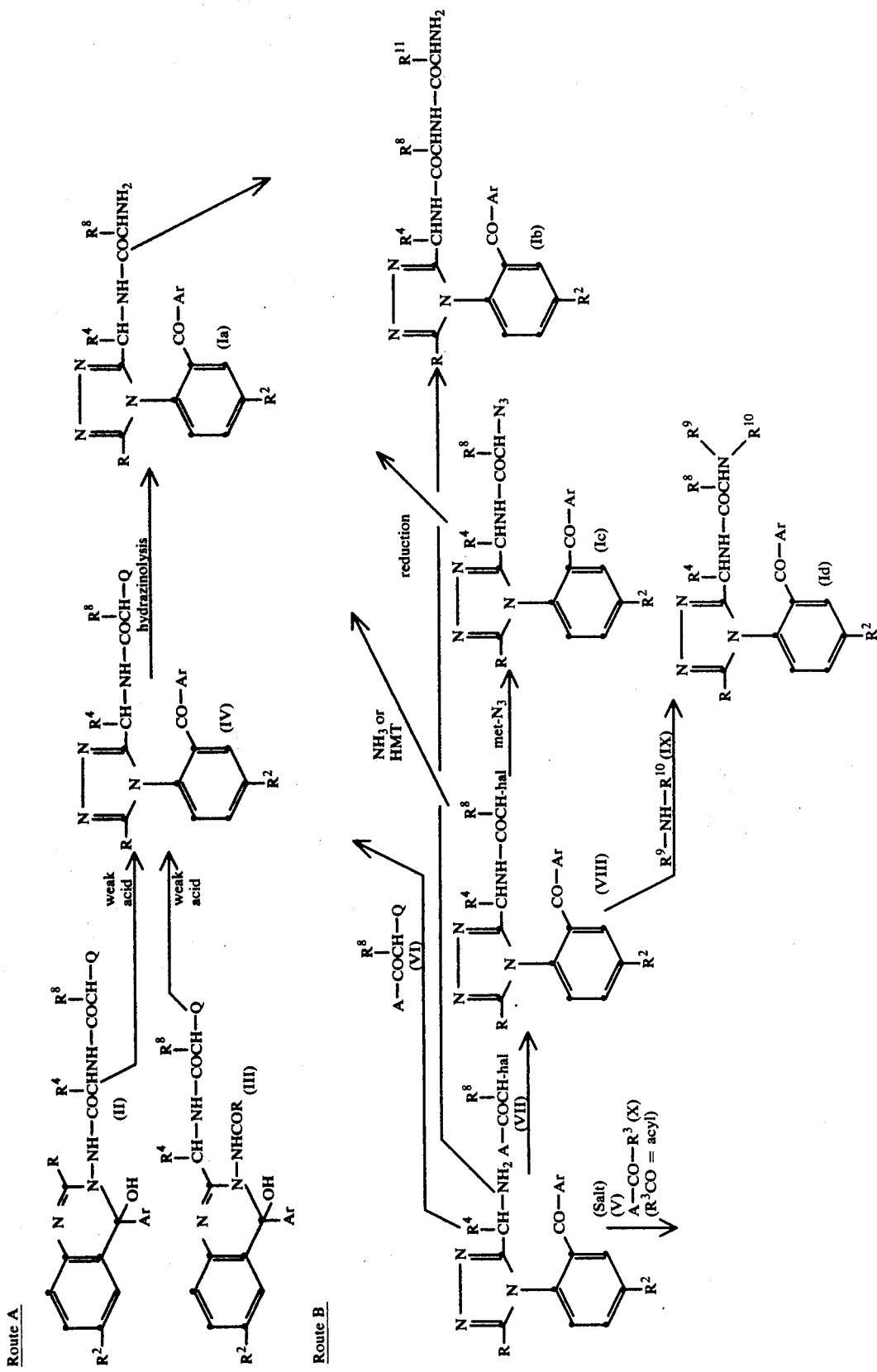

-continued
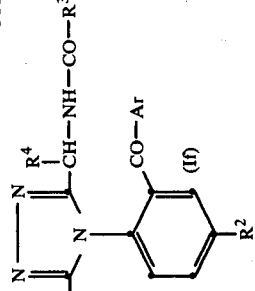
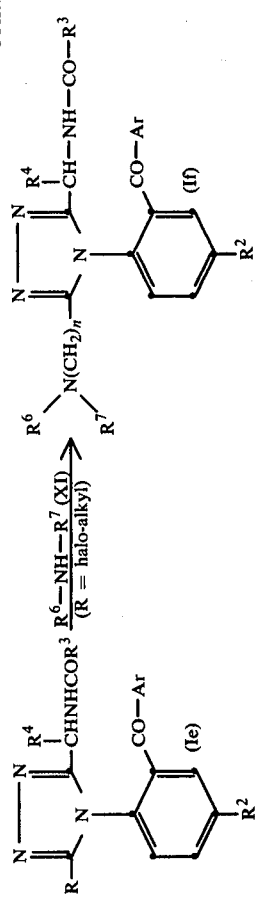

[wherein A represents a reactive group (e.g. halogen, an ester residue); Ar represents phenyl or 2-halogenophenyl; hal represents halogen; HMT represents hexamethylenetetramine; $R^{11}$ represents hydrogen, $C_1$-$C_6$ alkyl, or $C_7$-$C_{10}$ aralkyl; met represents alkali metal; Q represents phthalimido; and R, $R^2$, $R^4$, $R^6$, $R^7$, $R^8$, $R^9$, and $R^{10}$ each is as defined above.]

Preferred embodiments of the above routes are illustratively explained in the following description.

Route A

This route is effected by treating the quinazoline derivative (II) or (III) with a weak acid (e.g. acetic acid, monochloroacetic acid, propionic acid, benzoic acid, p-toluene-sulfonic acid) to give the phthalimide derivative (IV) and hydrazinolyzing the product (IV) to give the triazolylbenzophenone derivative (Ia). The first reaction can be carried out in general by using an excess of weak acid preferably without solvent at room temperature or under warming. Secondly, the hydrazinolysis of the phthalimide derivative (IV) can be carried out in a conventional manner such as by treating with hydrazine hydrate in a suitable solvent (e.g. ethanol, methanol, dimethylformamide, benzene, dimethylsulfoxide, chloroform) under heating. Hydrazinolysis can attain a high yield with a high purity of the product (Ia). Thirdly, the product (Ia) can be condensed with a phthalyl derivative of α-amino acid (e.g. glycine, phenyalanine, alanine, leucine) or its reactive derivative (e.g. chloride, ester) in a conventional manner for amino acid condensation such as in the presence of a condensing agent (e.g. dicyclohexylcarbodiimide) in a suitable inert solvent (e.g. dimethylformamide, dioxane, dimethylsulfoxide), and then the resultant phthalyl product is hydrazinolyzed as described above to give the second product (Ib). The starting quinazoline derivatives (II) and (III) can be derived, for example, from the aminobenzophenone derivative (XII) and the quinazoline derivative (XV) respectively:

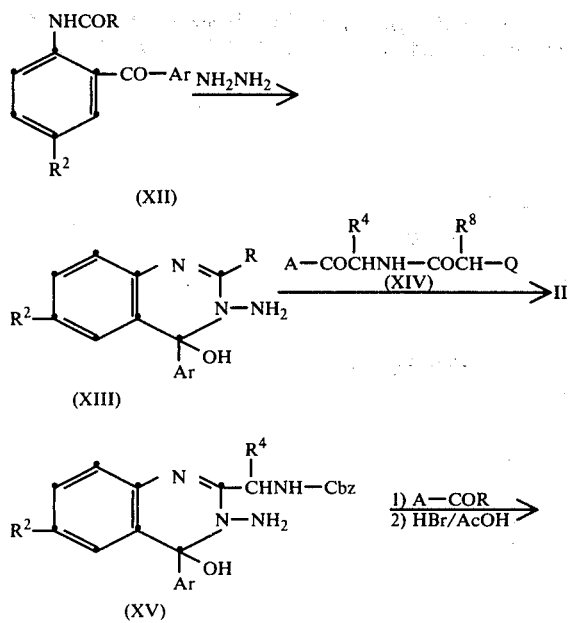

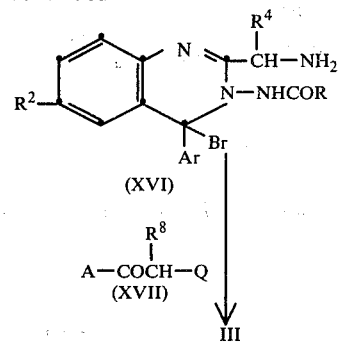

[wherein Cbz represents carbobenzoxy group; and A, Ar, Q, R, $R^2$, $R^4$, and $R^8$ each is as defined above].

Route B

The starting triazole (V), used in the form of a salt of an acid (e.g. hydrochloride, hydrobromide), is firstly reacted with a reactive derivative of α-halogenoacetic acid (VII). The reactive derivative means that the carboxy group has been converted to an active derivative, inclusive of acid halogenide, acid anhydride, acid azide and active ester. This reaction is effected in a conventional manner for forming the amido bond, such as in an inert solvent (e.g. dimethylformamide, hexamethylphosphoric triamide, pyridine) at room temperature or under cooling or heating. The resultant intermediate halide (VIII) can be converted into the product (Ia) of Route A by treating with ammonia or hexamethylenetetramine in a solvent (e.g. methanol, ethanol, diglyme, dimethylformamide) at room temperature or under warming; or by treating with alkali metal azide (e.g. sodium azide, potassium azide) in an inert solvent (e.g. dimethylformamide, dimethylsulfoxide, pyridine, chloroform) at room temperature or under warming, and reducing the resultant azido compound (Ic) with a reducing agent (e.g. stannous chloride in sodium hydroxide; zinc dust) or hydrogenating over a catalyst (e.g. Raney nickel, palladium carbon, platinum oxide) in a conventional manner such as in an inert solvent (e.g. methanol, ethanol, dimethylformamide, benzene, tetrahydrofuran) at room temperature or under cooling or heating.

Still, the intermediate halide (VIII) is reacted with an amine (IX) (e.g. methylamine, dimethylamine, diethylamine, pyrrolidine, morpholine, piperidine, γ-methylpiperazine) in an inert solvent (e.g. dimethylformamide, methanol, ethanol, acetone, hexamethylphosphoric triamide) at room temperature or under heating to give the product (Id).

Further, the starting triazole (V) is reacted with a reactive derivative of phthalyl-α-amino acid (VI) to give the phthalimide derivative (IV) described in said Route A; and the triazole (V) can be converted into the product (Ib) by condensing with a protected peptide (e.g. phthalyl-glycylglycine) and subjecting the resultant product to deprotection (e.g. hydrazinolysis) in a conventional manner.

The starting triazole (V) can be prepared, for example, from the aminobenzophenone (XVIII) as shown in the following scheme:

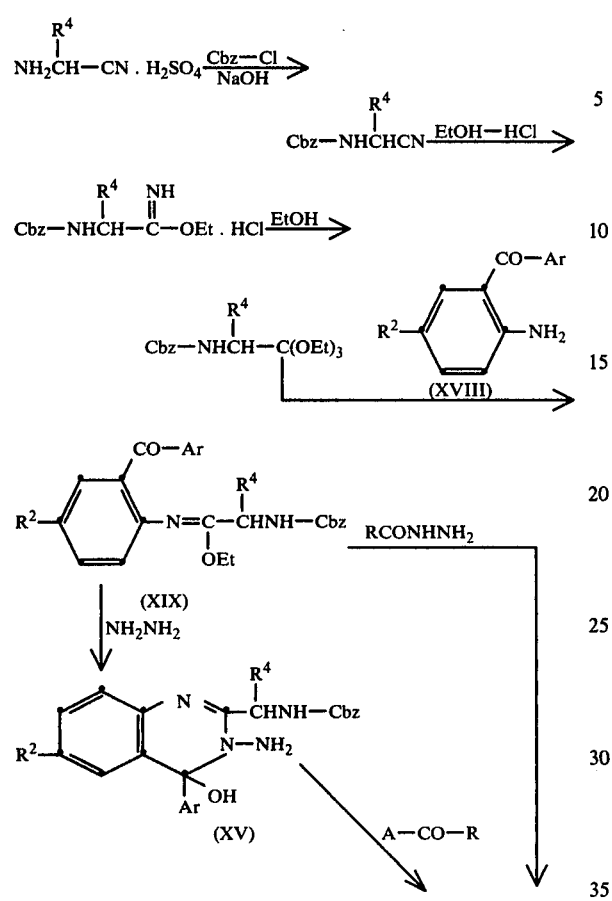

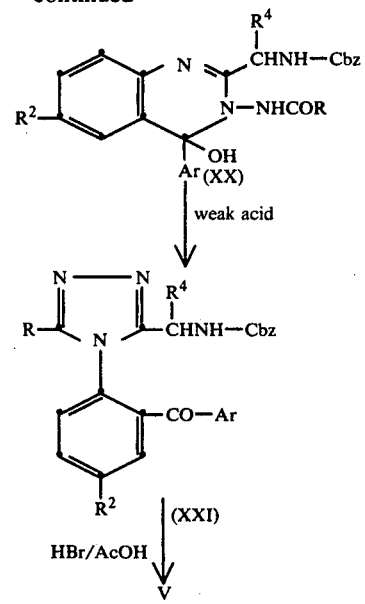

[wherein Ac represents acetyl; Et represents ethyl; and A, Ar, Cbz, R, $R^2$ and $R^4$ each is as defined above.]

Route C

The triazole (V) is reacted with the acylating agent (X) ($R^3CO$=acyl) in a conventional manner to give the product (Ie). Examples of the acylating agent are acetyl chloride, acetic anhydride, propionyl chloride, butyryl bromide, isobutyryl chloride, benzoyl chloride, and pyruvoyl chloride. If R of the product (Ie) is halo-alkyl, Ie can be further converted into the product (If) by treating with the amine (XI). This reaction is effected as in the step (VIII→Id) of Route B.

The starting compound (V) [R=halo-alkyl,

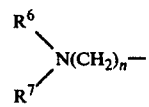

or $R^5$—X—$(CH_2)_n$—], used in Route B and Route C, can be prepared as shown in the following scheme:

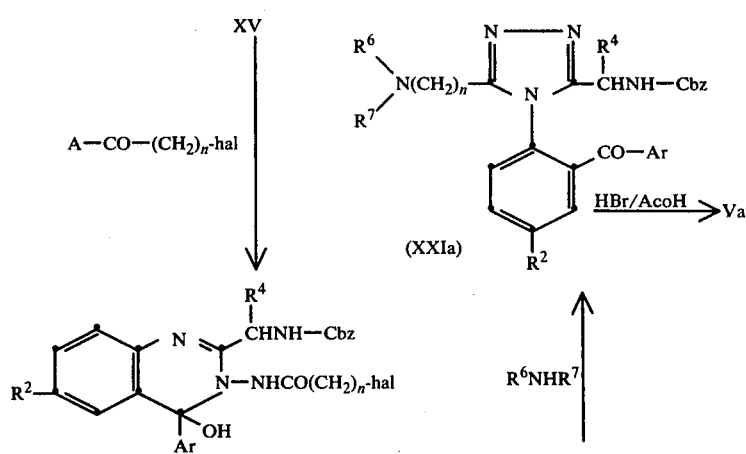

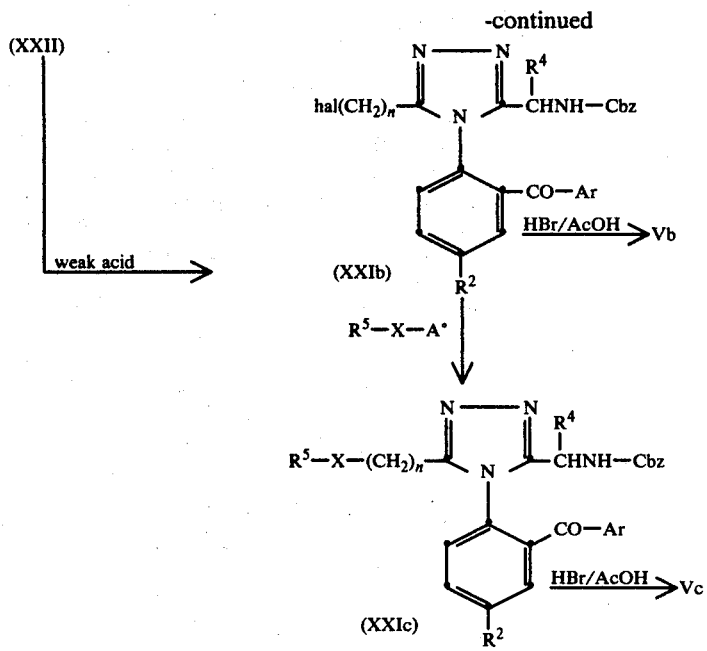

[wherein A° represents hydrogen, alkali metal, or active metal (e.g. silver, thallium); A, Ac, Ar, Cbz, $R^2$, $R^4$, $R^5$, X and n each is as defined above.]

The product (I) can be converted into its pharmaceutically acceptable acid addition salt such as that of inorganic acid (e.g. hydrochloric acid, hydrobromic acid, sulfuric acid, nitric acid, phosphoric acid, thiocyanic acid) or that of organic acid (e.g. acetic acid, succinic acid, oxalic acid, maleic acid, malic acid, phthalic acid, methanesulfonic acid, citric acid, toluenesulfonic acid, tartaric acid) for the necessity of preparation, crystallization, solubility, or improvement of stability.

Thus-obtained triazolylbenzophenone derivatives (I) or their pharmaceutically acceptable acid addition salts are useful as anxiolytics, sedatives, anticonvulsives, hypnotics, muscle relaxants, antidepressants, or their synthetic intermediates. For example, 2',5-dichloro-2-(3-glycylaminomethyl-5-methyl-4H-1,2,4-triazol-4-yl)-benzophenone showed $ED_{50}$ 0.23 mg/kg (mouse, per os) in the anticonvulsive activity against pentylenetetrazole, and $ED_{50}$ 0.25 mg/kg (mouse, per os) in the potentiating narcosis against thiopental sodium; and 2',5-dichloro-2-(3-glycylaminomethyl-5-dimethylaminomethyl-4H-1,2,4-triazol-4-yl)-benzophenone showed $ED_{50}$ 0.75 mg/kg (mouse, per os) in said anticonvulsive activity. The other triazolylbenzophenone derivatives (I) showed similar pharmacological activities.

The triazolylbenzophenone derivatives and their pharmaceutically acceptable acid addition salts are applied by either enteral or parenteral route singly or in combination with pharmaceutically suitable carriers such as wheat starch, corn starch, potato starch, gelatin, etc. The choice of carriers is determined by the preferred route of administration, the solubility of the substance, and standard pharmaceutical practice. Examples of pharmaceutical preparations are tablets, capsules, pills, suspensions, syrups, powders, and solutions. These compositions can be prepared in a conventional manner. A suitable dosage of the triazolylbenzophenone derivatives (I) or their pharmaceutically acceptable acid addition salts for human adults is on the order of about 0.2 mg to about 30 mg per day.

Still, the triazolylbenzophenone derivatives (I) or their acid addition salts are useful as growth promotors for domestic cattle and fowl.

Presently-preferred and practical embodiments of the present invention are illustratively shown in the following examples.

EXAMPLE 1

(1) To a solution of 2-phthalimidoacetyl chloride (1.5 g) in benzene (20 ml) and dimethylformamide (10 ml), 5-chloro-2-(3-aminomethyl-5-methyl-4H-1,2,4-triazol-4-yl)-benzophenone dihydrobromide ( 2.3 g) is added under ice cooling and stirring, and the temperature within the flask is gradually returned to room temperature. The reaction mixture is allowed to stand at room temperature, neutralized with saturated aqueous sodium bicarbonate, and shaken with ethyl acetate. The precipitated crystals are filtered, washed with methanol and dried to give 5-chloro-2-[2-phthalimidoacetamidomethyl)-5-methyl-4H-1,2,4-triazol-4-yl]-benzophenone (1.68 g) as crystals melting at 251°–253° C.

Anal. Calcd. for $C_{27}H_{20}N_5O_4Cl$: C, 63.10; H, 3.92; N, 13.62; Cl, 6.90. Found: C, 63.08; H, 4.03; N, 13.80; Cl, 7.07.

(2) To a solution of 5-chloro-2-[3-(2-phthalimidoacetamidomethyl)-5-methyl-4H-1,2,4-triazol-4-yl]-benzophenone (2.3 g) in ethanol (20 ml), hydrazine hydrate (0.92 g) is added, and the resultant mixture is refluxed for 1 hour. The precipitated phthalylhydrazide is filtered off, and the filtrate is evaporated under reduced pressure. The residue is dissolved in methylene chloride, washed with saturated aqueous sodium bicarbonate and water in order, dried over sodium sulfate, and evaporated under reduced pressure. The residue is chromatographed on a column of silica gel, and the product obtained from the eluate by evaporation is recrystallized from ethyl acetate to give 5-chloro-2-(3-glycylaminomethyl-5-methyl-4H-1,2,4-triazol-4-yl)-benzophenone hydrate as crystals melting at 110° to 113° C. The yield is 94%.

Anal. Calcd. for $C_{19}H_{18}N_5O_2Cl.H_2O$: C, 56.79; H, 5.01; N, 17.82; Cl, 8.80. Found: C, 57.12; H, 5.07; N, 17.52; Cl, 9.00.

Oxalate dihydrate, m.p. 112°–114° C. (recrystallized from water-acetonitrile).

EXAMPLE 2

(1) Using 2′,5-dichloro-2-(3-aminomethyl-5-methyl-4H-1,2,4-triazol-4-yl)-benzophenone dihydrobromide, the reaction is effected as in Example 1 (1), whereby 2′,5-dichloro-2-[3-(2-phthalimidoacetamidomethyl)-5-methyl-4H-1,2,4-triazol-4-yl]-benzophenone is obtained as crystals melting at 219°–231° C.

(2) Using 2′,5-dichloro-2-[3-(2-phthalimidoacetamidomethyl)-5-methyl-4H-1,2,4-triazol-4-yl]-benzophenone, the reaction is effected as in Example 1 (2), whereby 2′,5-dichloro-2-(3-glycylaminomethyl-5-methyl-1,2,4-triazol-4-yl)-benzophenone is obtained as crystals melting at 163° to 165° C.

Anal. Calcd. for $C_{19}H_{17}N_5O_2Cl_2$: C, 54.56; H, 4.10; N, 16.74; Cl, 16.95. Found: C, 54.37; H, 4.13; N, 16.45; Cl, 17.00.

Dihydrochloride monohydrate, m.p. 178.5°–181.5° C. (recrystallized from ethanol/ethyl acetate).

EXAMPLE 3

(1) To a solution of 5-chloro-2-(3-aminomethyl-5-methyl-4H-1,2,4-triazol-4-yl)-benzophenone dihydrobromide (0.5 g) in dimethylformamide (3 ml), chloroacetyl chloride (0.2 g) is dropwise added under ice cooling, and the resultant mixture is stirred. The reaction mixture is allowed to stand at room temperature overnight, mixed with water (3 ml), neutralized with aqueous sodium bicarbonate and shaken with methylene chloride. The methylene chloride layer is washed with water and saturated aqueous saline solution in order, dried over sodium sulfate, and evaporated under reduced pressure to remove the solvent. The residue is recrystallized from ethyl acetate/n-hexane to give 5-chloro-2-[3-(2-chloroacetamidomethyl)-5-methyl-4H-1,2,4-triazol-4-yl]-benzophenone (0.35 g) as crystals melting at 140° to 141° C.

(2) A suspension of 5-chloro-2-[3-(2-chloroacetamidomethyl)-5-methyl-4H-1,2,4-triazol-4-yl]-benzophenone (1.35 g) and potassium phthalimide (0.7 g) in dimethylformamide (10 ml) is warmed at 50° to 60° C. for 3 hours. The reaction mixture is shaken with methylene chloride. The methylene chloride layer is washed with water and saturated aqueous saline solution in order, dried over sodium sulfate and evaporated under reduced pressure to remove the solvent. The residue is crystallized from ethyl acetate/ether to give 5-chloro-2-[3-(2-phthalimido-acetamidomethyl)-5-methyl-4H-1,2,4-triazol-4-yl]-benzophenone as crystals melting at 251° to 253° C.

EXAMPLE 4

(1) Using 2′,5-dichloro-2-(3-aminomethyl-5-methyl-4H-1,2,4-triazol-4-yl)-benzophenone dihydrobromide, the reaction is carried out as in Example 3 (1), whereby 2′,5-dichloro-2-[3-(2-chloroacetamidomethyl)-5-methyl-4H-1,2,4-triazol-4-yl]-benzophenone is obtained as crystals melting at 151° to 153° C.

(2) Using the above product, the reaction is carried out as in Example 3 (2), whereby 2′,5-dichloro-[3-(2-phthalimidoacetamidomethyl)-5-methyl-4H-1,2,4-triazol-4-yl]-benzophenone is obtained as crystals melting at 219° to 231° C.

EXAMPLE 5

To a solution of 5-chloro-2-[3-(2-chloroacetamidomethyl)-5-methyl-4H-1,2,4-triazol-4-yl]-benzophenone (0.4 g) in methanol (4 ml) and chloroform (8 ml), 40% aqueous dimethylamine (0.5 g) is added, and the resultant mixture is stirred at room temperature for 24 hours. The reaction mixture is evaporated under reduced pressure, and the residue is shaken with methylene chloride (20 ml). The methylene chloride layer is washed with aqueous sodium bicarbonate and water in order, dried over sodium sulfate and evaporated under reduced pressure to remove the solvent. The residue is chromatographed on a column of silica gel, whereby 5-chloro-2-[3-(2-dimethylaminoacetamidomethyl)-5-methyl-4H-1,2,4-triazol-4-yl]-benzophenone is obtained as a colorless oil.

NMR (CDCl$_3$), δ, 2.10 (s., CH$_3$), 2.23 (s., N(CH$_3$)$_2$), 2.86 (s., COCH$_2$N=), 4.36 (ABX, CH$_2$NHCO).

Oxalate hydrate, m.p. 176.5°–177.5° C. (recrystallized from ethanol).

Anal. Calcd. for $C_{21}H_{22}N_5O_2Cl.(COOH)_2.H_2O$: C, 53.13; H, 5.04; N, 13.46; Cl, 6.81. Found: C, 53.54; H, 5.07; N, 13.02; Cl, 6.83.

EXAMPLES 6 TO 10

Using the following starting material (V), the reaction is carried out as in Example 5, whereby the corresponding product (Id) is obtained:

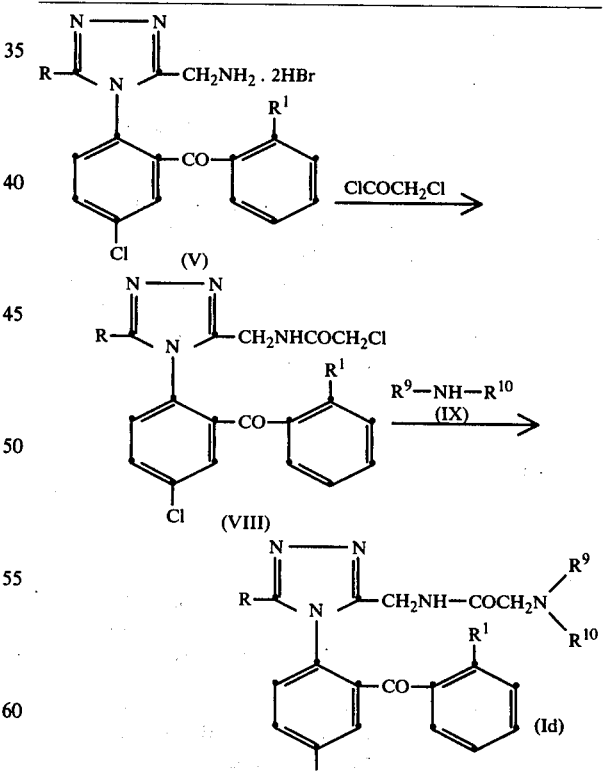

| Ex. No. | V | | VIII | | Id |
|---|---|---|---|---|---|
| | R | R$^1$ | R$^9$ | R$^{10}$ | m.p. (° C) or IR (cm$^{-1}$) |
| 6 | Me | Cl | Me | Me | 148–148.5 |
| 7 | Me | H | Et | Et | 60 (bubbling, citrate) |
| 8 | Me | Cl | Et | Et | 136.5–137.5 |
| 9 | Me | H | Me | H | 187–188 (oxalate) |
| 10 | Me | Cl | Me | H | Oil, 3320(NH), 1670(CO) |

-continued

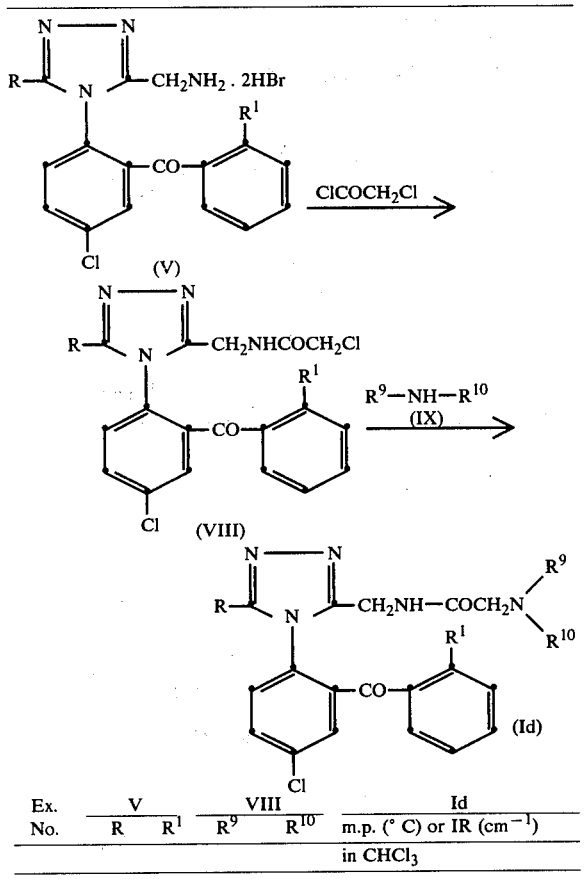

| Ex. No. | V | | VIII | | Id | |
|---|---|---|---|---|---|---|
| | R | R¹ | R⁹ | R¹⁰ | m.p. (° C) or IR (cm⁻¹) in CHCl₃ | |

Note:
The abbreviations each has the following significance: Me (Methyl), Et (ethyl), H (hydrogen), Cl (chlorine), m.p. (melting point), IR (infra-red absorption spectre).

EXAMPLE 11

(1) A solution of 3-(N$^\alpha$-carbobenzoxyglycyl-glycylamino)-4-hydroxy-4-phenyl-6-chloro-3,4-dihydroquinazoline (1.5 g) in acetic acid (20 ml) is refluxed with heating for 2 hours. The reaction mixture is evaporated under reduced pressure, and the residue is dissolved in ethyl acetate (30 ml). The ethyl acetate layer is washed with aqueous sodium bicarbonate and water in order, dried over sodium sulfate and evaporated under reduced pressure to remove the solvent. The residue is chromatographed on a column of silica gel, which is eluted with ethyl acetate/methanol to give 5-chloro-2-[3-(N-carbobenzoxyglycyl)aminomethyl-4H-1,2,4-triazol-4-yl]-benzophenone as a colorless oil (0.515 g).

IR (CHCl₃), 3400, 3280, 1720, 1680 cm⁻¹.

NMR (CDCl₃), δ, 3.8 (broad, d., C$\underline{H}_2$NHCOO), 4.2 (broad, d., C$\underline{H}_2$-NH), 5.1 (s., (COOC$\underline{H}_2$C₆H₅).

(2) To a solution of 5-chloro-2-[3-(N-carbobenzoxyglycyl)aminomethyl-4H-1,2,4-triazol-4-yl]-benzophenone (2.1 g) in anisole (4 ml), 30% hydrogen bromide-acetic acid is added. The resultant mixture is stirred for 1 hour and mixed with ether. The precipitate is filtered, washed with ether and dissolved in methylene chloride (20 ml). The methylene chloride layer is washed with saturated aqueous sodium bicarbonate, water and saturated aqueous saline solution in order, dried over sodium sulfate and evaporated under reduced pressure to remove the solvent. The residue is chromatographed on a column of silica gel, which is eluted with methanol to give 5-chloro-2-(3-glycylaminomethyl-4H-1,2,4-triazol-4-yl)-benzophenone as a colorless oil (0.39 g).

IR (CHCl₃), 3330, 1670, 1595 cm⁻¹.

NMR (CDCl₃), δ, 1.70 (broad m., NH₂), 3.27 (broad m., COC$\underline{H}_2$NH₂), 4.47 (ABX, C$\underline{H}_2$NH), 8.07 (s., (—N=CH—N=).

Oxalate, m.p. 140° C. (bubbling).

Anal. Calcd. for $C_{18}H_{16}N_5O_2Cl \cdot 2^3$ (COOH)$_2 \cdot 2^3 H_2O$: C, 47.42; H, 4.17; N, 13.16; Cl, 6.67. Found: C, 47.54; H, 4.12; N, 13.40; Cl, 6.69.

EXAMPLE 12

(1) A solution of 3-[N$^\alpha$-(2-phthalimidoacetyl)-glycylamino]-4-hydroxy-4-phenyl-6-chloro-3,4-dihydroquinazoline (0.7 g) in acetic acid (5 ml) is refluxed with heating for 2.5 hours. The reaction mixture is evaporated under reduced pressure, and the residue is dissolved in ethyl acetate. The ethyl acetate layer is washed with saturated aqueous sodium bicarbonate and water in order, dried over sodium sulfate, and evaporated under reduced pressure to remove the solvent. The residue is chromatographed on a column of silica gel, which is eluted with ethyl acetate-methanol (20:1) to give 5-chloro-2-[3-(2-phthalimidoacetamidomethyl)-4H-1,2,4-triazol-4-yl]benzophenone as crystals melting at 214° to 215° C.

IR (CHCl₃), 1780, 1720, 1690 cm⁻¹.

(2) Using 5-chloro-2-[3-(2-phthalimidoacetamidomethyl)-4H-1,2,4-triazol-4-yl]-benzophenone, the reaction is effected as in Example 1 (2), whereby 5-chloro-2-(3-glycylaminomethyl-4H-1,2,4-triazol-4-yl)-benzophenone is obtained as colorless oil.

EXAMPLE 13

(1) To a solution of 2',5-dichloro-2-[3-(2-chloroacetamidomethyl)-5-methyl-4H-1,2,4-triazol-4-yl]-benzophenone (1.533 g) in dimethylformamide (15 ml), sodium azide (0.228 g) is added portionwise, and the resultant mixture is stirred at room temperature for 2.25 hours and allowed to stand overnight. The reaction mixture is evaporated under reduced pressure to remove the solvent, and the residue is shaken with chloroform. The organic layer is washed with water, dried and evaporated to remove the chloroform. The residue is washed with ether to give 2',5-dichloro-2-[3-(2-azidoacetamidomethyl)-5-methyl-4H-1,2,4-triazol-4-yl]-benzophenone (1.45 g). The yield is 93.2%.

IR (Nujol), 2100 cm⁻¹ (N₃).

NMR (CDCl₃), δ 2.23 (s., CH₃), 3.9 (S., CH₂N₃), 4.20 (ABX, C$\underline{H}_2$NH), 8.37 (m., NH).

(2) To a suspension of the above product (0.382 g) in 95% ethanol (10 ml), a solution of stannous chloride dihydrate (0.29 g) in 2N sodium hydroxide (4.1 ml) is added dropwise at 0° to 4° C. The reaction mixture is shaken with chloroform. The organic layer is evaporated under reduced pressure to remove the chloroform. The residue is washed with ether to give 2',5-dichloro-2-(3-glycylaminomethyl-5-methyl-4H-1,2,4-triazol-4-yl)-benzophenone (0.33 g). The yield is 91%.

EXAMPLE 14

(1) A mixture of 5-chloro-2-[3-(N-carbobenzoxyaminomethyl)-5-chloromethyl-4H-1,2,4-triazol-4-yl]-benzophenone (0.995 g) and 30% hydrogen bromide-acetic acid (2 ml) is stirred at room temperature for 1.25 hours, and the mixture is washed with ether (50 ml) twice. The obtained free base is mixed with benzene (10 ml), acetyl chloride (0.5 g) and dimethylformamide (6 ml), and the resultant mixture is stirred at room temperature for 2 hours, and allowed to stand overnight. The reaction mixture is neutralized with aqueous sodium bicarbonate, and the precipitated crystals are filtered and washed with ether and chloroform in order to give 5-chloro-2-(3-acetamidomethyl-5-chloromethyl-4H-1,2,4-triazol-4-yl)-benzophenone (0.6 g) as crystals melting at 193° to 199° C. (decomp.).

Anal. Calcd. for $C_{19}H_{16}N_4Cl_2O_2 \cdot H_2O$: C, 54.16; H, 4.31; N, 13.30; Cl, 16.83. Found: C, 54.57; H, 4.05; N, 13.01; Cl, 17.00.

U.V. $\lambda_{max}^{EtOH}$ (log ε) 259 mμ (4.110).

(2) To a suspension of the above product (0.54 g) in ethanol (10 ml), aqueous 40% dimethylamine (1.2 ml) is added, and the resultant mixture is stirred at room temperature for 1 hour. Then, dimethylformamide (6 ml) is added to the mixture, which is stirred for 3 hours and allowed to stand overnight. The reaction mixture is evaporated under reduced pressure, and the residue is crystallized from water. The precipitate is filtered and recrystallized from ethyl acetate to give 5-chloro-2-(3-acetamidomethyl-5-dimethylaminomethyl-4H-1,2,4-triazol-4-yl)-benzophenone (0.35 g).

Anal. Calcd. for $C_{21}H_{22}N_5O_2Cl$: C, 61.24; H, 5.38; N, 17.00; Cl, 8.61. Found: C, 60.80; H, 5.61; N, 16.55; Cl, 8.70.

UV $\lambda_{max}^{EtOH}$ (log ε), 257 mμ (4.141).

EXAMPLES 15 TO 16

Using the following reagent (X), the reaction is effected as in Example 14, whereby the following product (Ie, If) are obtained:

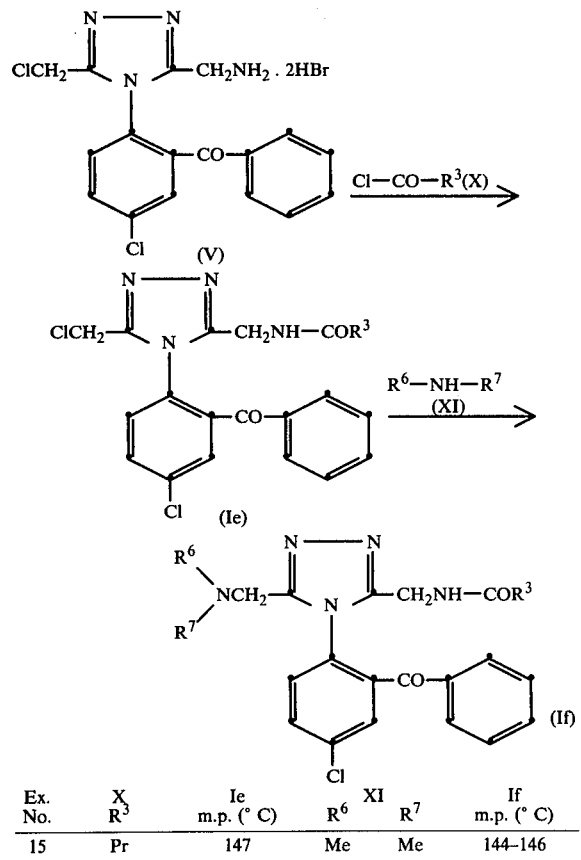

| Ex. No. | X R³ | Ie m.p. (° C) | XI R⁶ | R⁷ | If m.p. (° C) |
|---|---|---|---|---|---|
| 15 | Pr | 147 | Me | Me | 144–146 |

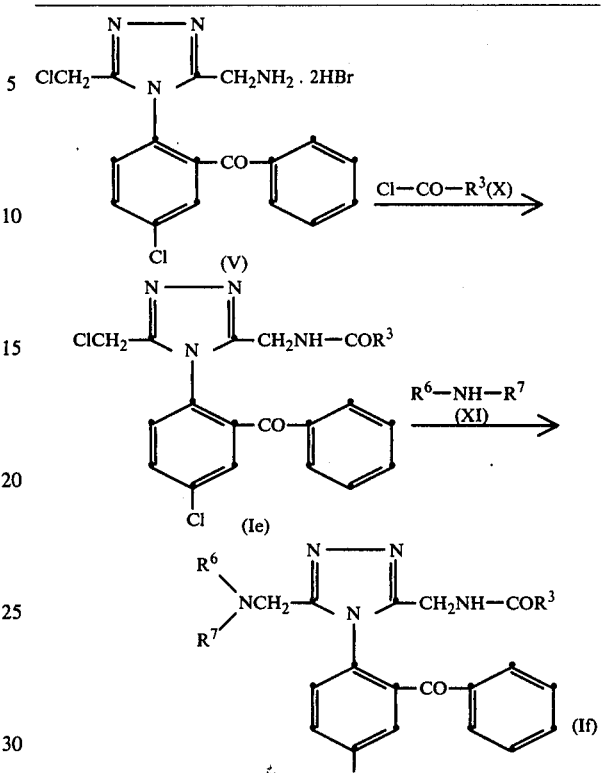

| Ex. No. | X R³ | Ie m.p. (° C) | XI R⁶ | R⁷ | If m.p. (° C) |
|---|---|---|---|---|---|
| 16 | p-Met—Ph | 137–138 | Me | Me | 164–165 |

Note:
The abbreviations each has the following significance: Met (methoxy), Ph (phenyl).

EXAMPLE 17

A solution of pyruvic acid (0.33 g) and thionyl chloride (0.27 g) in chloroform (2 ml) is refluxed for 1 hour. After cooling, the solution is mixed with 2',5-dichloro-3-(3-aminomethyl-5-methyl-4H-1,2,4-triazol-4-yl)-benzophenone dihydrobromide (1.31 g), benzene (6 ml) and dimethylformamide (11 ml) at 0° C. The resultant mixture is stirred at room temperature for 3 hours and allowed to stand overnight. The reaction mixture is neutralized with aqueous sodium bicarbonate and shaken with ethyl acetate. The organic layer is washed with water, dried and evaporated to remove the solvent. The residue is recrystallized from ethyl acetate to give 2',5-dichloro-3-(3-pyruvamidomethyl-5-methyl-4H-1,2,4-triazol-4-yl)-benzophenone (0.7 g) as crystals melting at 178° to 180° C.

Anal. Calcd. for $C_{20}H_{16}N_4Cl_2O_3$: C, 55.70; H, 3.74; N, 12.99; Cl, 16.44. Found: C, 55.63; H, 3.79; N, 12.95; Cl, 16.30.

UV $\lambda_{max}^{EtOH}$ (log ε) 215, 253, 290 mμ (4.533, 4.022, 3.398).

EXAMPLE 18

(1) To a solution of 2-carbobenzoxyaminomethyl-3-amino-4-hydroxy-4-(2-chlorophenyl)-6-chloro-3,4-dihydroquinazoline (2.36 g) in dimethylformamide (15 ml), acetyl chloride (0.79 g) is added, and the resultant mixture is stirred at room temperature for 5 hours and allowed to stand overnight. The reaction mixture is neutralized with aqueous sodium bicarbonate and shaken with ethyl acetate. The organic layer is washed with water and evaporated to give 2-carbobenzoxyaminomethyl-3-acetamido-4-hydroxy-4-(2-chlorophenyl)-6-chloro-3,4-dihydroquinazoline (2.1 g).

(2) A mixture of the above product (2.7 g) and 30% hydrogen bromide-acetic acid (6 ml) is stirred at room temperature for 1½ hours. The reaction mixture is washed with ether to give 2-aminomethyl-3-acetamido-4-bromo-4-(2-chlorophenyl)-6-chloro-3,4-dihydroquinazoline dihydrobromide dihydrate (2.85 g) as crystals melting at 169° to 175° C. (decomp.).

Anal. Calcd. for $C_{17}H_{15}N_4Cl_2BrO\cdot 2HBr\cdot 2H_2O$: C, 32.00; H, 3.32; N, 8.78; Cl, 11.11; Br, 37.26. Found: C, 32.28; H, 3.11; N, 8.99; Cl, 11.40; Br, 37.54.

(3) To a solution of 2-phthalimidoacetyl chloride (1.65 g) in hexamethylphosphoric triamide (20 ml), the above product (2.3 g) is added, and the resultant mixture is stirred at room temperature for 3 hours. The reaction mixture is mixed with ether and neutralized with aqueous sodium bicarbonate. The precipitate is filtered and shaken with chloroform. The chloroform layer is evaporated to remove the chloroform, and the residue is treated with ether to give 2-(2-phthalimidoacetamidomethyl)-3-acetamido-4-hydroxy-4-(2-chlorophenyl)-6-chloroquinazoline (1.15 g). This substance is recrystallized from ethyl acetate to give crystals melting at 165° to 168° C.

Anal. Calcd. for $C_{27}H_{21}N_5O_5Cl_2$: C, 57.26; H, 3.74; N, 12.36; Cl, 12.52. Found: C, 57.33; H, 4.01; N, 11.73; Cl, 12.15.

UV $\lambda_{max}^{EtOH}$ (log ε) 219, 286 mμ (4.852, 4.141).

(4) A solution of the above product (1.15 g) in acetic acid (11 ml) is refluxed for 2.5 hours, and the reaction mixture is evaporated to remove the acetic acid. The residue is shaken with chloroform. The chloroform layer is washed with aqueous sodium bicarbonate and water in order, dried and evaporated to remove the chloroform. The residue is treated with ethyl acetate to give 2′,5-dichloro-2-[3-(2-phthalimidoacetamidomethyl)-5-methyl-4H-1,2,4-triazol-4-yl]-benzophenone (0.4 g).

(5) The above product is treated with hydrazine hydrate as in Example 1 (2), whereby 2′,5-dichloro-2-(3-glycylaminomethyl-5-methyl-4H-1,2,4-triazol-4-yl)-benzophenone is obtained.

EXAMPLE 19

(1) To a mixture of hexamethylphosphoric triamide (12 ml) and chloroacetyl chloride (0.452 g), 2-aminomethyl-3-acetamido-4-bromo-4-(2-chlorophenyl)-6-chloro-3,4-dihydroquinzaoline dihydrobromide dihydrate (1.276 g) is added, and the resultant mixture is stirred at room temperature for 5 hours. The reaction mixture is mixed with ether and washed with aqueous sodium bicarbonate and water in order. The precipitate is dried to give 2-(2-chloroacetamidomethyl)-3-acetamido-4-hydroxy-4-(2-chlorophenyl)-6-chloro-3,4-dihydroquinazoline (0.63 g). This product (0.6 g) is dissolved in acetic acid (6 ml) to give a solution, which is refluxed for 2 hours. The reaction mixture is evaporated under reduced pressure. The residue is extracted with ethyl acetate. The organic layer is washed with aqueous sodium bicarbonate and water in order, dried and evaporated to remove the ethyl acetate. The residue is chromatographed on a column of silica gel, which is eluted with methanol to give 2′,5-dichloro-2-[3-(2-chloroacetamidomethyl)-5-methyl-4H-1,2,4-triazol-4-yl]-benzophenone (0.15 g).

(2) A mixture of the above product (0.86 g) and 15% ammonia-methanol (15 ml) is allowed to stand at room temperature for 3 days, and the reaction mixture is evaporated to remove the solvent. The residue is chromatographed on a column of silica gel, which is eluted with methanol to give 2′,5-dichloro-2-(3-glycylaminomethyl-5-methyl-4H-1,2,4-triazol-4-yl)-benzophenone (0.42 g).

EXAMPLE 20

(1) To a solution of 2-carbobenzoxyaminomethyl-3-amino-4-hydroxy-4-(2-chlorophenyl)-6-chloro-3,4-dihydroquinazoline (18.84 g) in dimethylformamide (100 ml), chloroacetyl chloride (8.48 g) is added, and the resultant mixture is stirred at room temperature for 1 hour and allowed to stand overnight. The reaction mixture is neutralized with aqueous sodium bicarbonate and shaked with ethyl acetate. The ethyl acetate layer is evaporated under reduced pressure to remove the solvent, and the residue is washed with ether to give 2-carbobenzoxyaminomethyl-3-(2-chloroacetamido)-4-hydroxy-4-(2-chlorophenyl)-6-chloro-3,4-dihydroquinazoline (18.9 g). This product is recrystallized from ethyl acetate to give crystals melting at 130° to 134° C.

Anal. Calcd. for $C_{25}H_{21}N_4Cl_3O_4$: C, 54.81; H, 3.86; N, 10.23; Cl, 19.41. Found: C, 54.78; H, 3.66; N, 10.09; Cl, 19.38.

UV $\lambda_{max}^{EtOH}$ (log ε) 247, 285 mμ (3.919, 4.098).

(2) A solution of the above product (0.75 g) in acetic acid (7 ml) is refluxed for 1.5 hours and evaporated under reduced pressure to remove the acetic acid. The residue is neutralized with aqueous sodium bicarbonate and shaken with ethyl acetate. The organic layer is washed with water, dried and evaporated under reduced pressure. The residue is treated with ether to give 2′,5-dichloro-2-(3-carbobenzoxyaminomethyl-5-chloromethyl-4H-1,2,4-triazol-4-yl)-benzophenone (0.65 g). This product is recrystallized from ethyl acetate to give crystals melting at 170° to 171° C.

Anal. Calcd. for $C_{25}H_{19}N_4Cl_3O_3$: C, 56.68; H, 3.61; N, 10.57; Cl, 20.07. Found: C, 56.69; H, 3.76; N, 10.34; Cl, 20.14.

UV $\lambda_{max}^{EtOH}$ (log ε) 255, 293 mμ (3.984, 3.831).

(3) A solution of the above product (1.32 g) in 30% hydrogen bromide-acetic acid (2.5 ml) is stirred at room temperature for 1 hour. The reaction mixture is washed with ether (50 ml) twice, and the residue is mixed with chloroacetyl chloride (0.8 g), benzene (15 ml) and dimethylformamide (8 ml). The resultant mixture is stirred at room temperature for 4 hours. The reaction mixture is neutralized with aqueous sodium bicarbonate and shaken with ethyl acetate. The organic layer is washed with water, dried, and evaporated under reduced pressure to remove the solvent. The residue is dissolved in methanol (20 ml) to give a solution, which is mixed with 1-methylpiperazine (1.76 g) and potassium iodide (0.145 g). The resultant mixture is stirred at room temperature for 1.5 hours, allowed to stand overnight and refluxed for 4 hours. The reaction mixture is evaporated under reduced pressure to remove the solvent, and the residue is shaken with chloroform. The chloroform layer is washed with water, dried and evaporated under reduced pressure to remove the chloroform, whereby 2′,5-dichloro-2-[3-(2-γ-methyl-piperazinoacetamido-methyl)-5-γ-methyl-piperazinomethyl-4H-1,2,4-triazol-4-yl]-benzophenone (1.5 g) is obtained as an oil.

NMR (CDCl₃), δ, 3.0 (s., COCH₂N), 3.5 (s.,

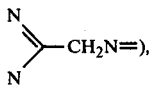

4.33 (ABX, CH₂NH), 7.80 (m., NH).

EXAMPLE 21

Using diethylamine in lieu of 1-methylpiperazine, the reaction is effected as in Example 20 (3), 2′,5-dichloro-2-[3-(2-diethylaminoacetamidomethyl)-5-diethylaminomethyl-4H-1,2,4-triazol-4-yl]-benzophenone is obtained as an oil. The yield is 88%.

NMR (CDCl₃), δ, 0.72 (t., J=14,

1.0 (t., J=14, COCH₂N(CH₂CH₃)₂, 2.97 (s., COCH₂NEt₂), 3.5 (s.,

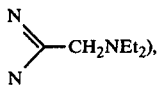

4.14 (ABX, CH₂NH), 8.0 (m., NH).

EXAMPLE 22

(1) To a solution of 2′,5-dichloro-2-(3-carbobenzoxyaminomethyl-5-chloromethyl-4H-1,2,4-triazol-4-yl)-benzophenone (1.32 g) in methanol (20 ml) and chloroform (20 ml), potassium iodide (0.4 g) and diethylamine (3 ml) are added, and the resultant mixture is refluxed for 5 hours. The reaction mixture is evaporated under reduced pressure to remove the solvent, and the residue is extracted with ethyl acetate. The ethyl acetate layer is washed with water, dried, and evaporated under reduced pressure to remove the ethyl acetate. The residue is treated with ether to give 2′,5-dichloro-2-(3-carbobenzoxyaminomethyl-5-diethylaminomethyl-4H-1,2,4-triazol-4-yl)-benzophenone (1.1 g). The product is recrystallized from ether-ethyl acetate to give crystals melting at 89° to 94° C.

(2) A mixture of the above product (1.41 g) and 30% hydrogen bromide-acetic acid (2.5 ml) is stirred at room temperature for 2 hours and washed with ether (50 ml) twice. The free base is mixed with benzene (15 ml), 2-phthalimidoacetyl chloride (1.12 g) and dimethylformamide (8 ml) in order, and the resultant mixture is stirred at room temperature for 2 hours and allowed to stand overnight. The reaction mixture is mixed with ethyl acetate, neutralized with aqueous sodium bicarbonate. The ethyl acetate layer is washed with water, dried and evaporated under reduced pressure to remove the solvent. The residue is treated with ether to give 2′,5-dichloro-2-[3-(2-phthalimidoacetamidomethyl)-5-diethylaminomethyl-4H-1,2,4-triazol-4-yl]-benzophenone (1.4 g). The product is recrystallized from ethanol to give crystals melting at 212° to 214° C.

UV $\lambda_{max}^{EtOH}$ (log ε) 218.5, 294 mμ (4.85, 3.954).

(3) A suspension of the above product (1.12 g) and hydrazine hydrate (0.234 g) in ethanol (10 ml) is refluxed for 25 minutes. The precipitate is filtered off, and the filtrate is evaporated under reduced pressure to remove the ethanol. The residue is extracted with ethyl acetate. The ethyl acetate layer is washed with aqueous sodium bicarbonate and water in order, dried, and evaporated under reduced pressure to remove the solvent. The residue is chromatographed on a column of silica gel, which is eluted with methanol to give 2′,5-dichloro-2-(3-glycylaminomethyl-5-diethylaminomethyl-4H-1,2,4-triazol-4-yl)-benzophenone (0.8 g) as an oil.

NMR (CDCl₃), δ, 0.73 (t., J=15, CH₂CH₃), 3.53 (s., CH₂NEt₂), 4.37 (ABX, NHCH₂), 8.13 (br., NH₂).

EXAMPLE 23

Using dimethylamine in lieu of diethylamine, the reaction is effected as in Example 22, whereby the following products are obtained:

(1) 2′,5-dichloro-2-(3-carbobenzoxyaminomethyl-5-dimethylaminomethyl-4H-1,2,4-triazol-4-yl)-benzophenone, m.p. 123°–125° C. (recrystallized from ethyl acetate); UV $\lambda_{max}^{EtOH}$ (log ε) 253, 291 mμ (4.01, 3.837).

(2) 2′,5-dichloro-2-[3-(2-phthalimidoacetamidomethyl)-5-dimethylaminomethyl-4H-1,2,4-triazol-4-yl]-benzophenone, m.p. 226°–227° C. (recrystallized from ethanol);

(3) 2′,5-dichloro-2-(3-glycylaminomethyl-5-dimethylaminomethyl-4H-1,2,4-triazol-4-yl)-benzophenone, m.p. 179°–183° C. (recrystallized from ethyl acetate); UV $\lambda_{max}^{EtOH}$ (log ε) 214, 250, 290 mμ (4.056, 3.984, 3.438).

EXAMPLE 24

(1) To a suspension of sodium hydroxide (0.08 g) in dimethylformamide (8 ml), thiophenol (0.33 g) is added under ice-cooling, and the resultant mixture is stirred under ice-cooling for 5 minutes. 2′,5-Dichloro-2-(3-carbobenzoxyaminomethyl-5-chloromethyl-4H-1,2,4-triazol-4-yl)-benzophenone (1.06 g) is added to the mixture, which is stirred at room temperature for 2.5 hours. The reaction mixture is shaken with ethyl acetate, and the ethyl acetate layer is washed with water, dried, and evaporated under reduced pressure to remove the solvent. The residue is washed with n-hexane to give a gelatinous product, which is mixed with 30% hydrogen bromide-acetic acid (2.4 ml). The mixture is stirred at room temperature for 2 hours and washed with ether. The resultant crystals are filtered, washed with ether (50 ml), and mixed with benzene (10 ml), 2-phthalimidoacetyl chloride (0.672 g), and dimethylformamide (7 ml) in order. The mixture is stirred at room temperature for 3 hours and shaken with ethyl acetate. The ethyl acetate layer is washed with aqueous sodium bicarbonate and water in order, dried, and evaporated under reduced pressure to remove the solvent, whereby 2′,5-dichloro-2-[3-(2-phthalimidoacetamidomethyl)-5-phenylthiomethyl-4H-1,2,4-triazol-4-yl]-benzophenone (1.05 g). The product is recrystallized from ethanol to give crystals melting at 220° to 221° C.

UV $\lambda_{max}^{EtOH}$ (log ε) 219, 290 mμ (4.902, 3.702).

(2) A suspension of the above product (0.84 g) and hydrazine hydrate (0.196 g) in ethanol (9 ml) is refluxed for 30 minutes, and the precipitate is filtered off. The filtrate is evaporated under reduced pressure to remove the solvent, and the residue is extracted with ethyl acetate. The ethyl acetate layer is washed with aqueous sodium bicarbonate and water in order, dried, and evaporated under reduced pressure to remove the solvent. The residue is chromatographed on a column of silica gel, which is eluted with methanol to give 2',5-dichloro-2-(3-glycylaminomethyl-5-phenylthiomethyl-4H-1,2,4-triazol-4-yl)-benzophenone (0.55 g) as powder.

Anal. Calcd. for $C_{25}H_{21}N_5Cl_2SO_2.\frac{1}{4}H_2O$: C, 56.55; H, 4.08; N, 13.19; Cl, 13.35; S, 6.04. Found: C, 56.58; H, 4.18; N, 12.84; Cl, 12.87; S, 6.06.

UV $\lambda_{max}^{EtOH}$ (log ε) 253 mμ (4.137).

EXAMPLE 25

Using propyl mercaptan in lieu of thiophenol, the reaction is effected as in Example 24, whereby the following products are obtained:

(1) 2',5-dichloro-2-[3-(2-phthalimidoacetamidomethyl)-5-propylthiomethyl-4H-1,2,4-triazol-4-yl]-benzophenone, m.p.172°–184° C. (recrystallized from ethanol); Anal. Calcd. for $C_{30}H_{25}N_5SCl_2O_4.\frac{1}{2}H_2O$: C, 57.05; H, 4.15; N, 11.09; Cl, 11.23; S, 5.08. Found: C, 57.21; H, 4.39; N, 10.72; Cl, 11.54; S, 5.17.

(2) 2',5-dichloro-2-(3-glycylaminomethyl-5-propylthiomethyl-4H-1,2,4-triazol-4-yl)-benzophenone oxalate dihydrate, m.p. 109°–113° C. (recrystallized from dilute acetonitrile);

Anal. Calcd. for $C_{22}H_{23}N_5SCl_2O_2.(COOH)_2.2H_2O$: C, 46.61; H, 4.73; N, 11.32; Cl, 11.46; S, 5.18. Found: C, 46.85; H, 4.39; N, 10.96; Cl, 11.33; S, 5.74.

EXAMPLE 26

Using pyrrolidine in lieu of diethylamine, the reaction is effected as in Example 22, whereby the following products are obtained:

(1) 2',5-dichloro-2-(3-carbobenzoxyaminomethyl-5-pyrrolidinomethyl-4H-1,2,4-triazol-4-yl)-benzophenone, m.p. 143°–145° C. (recrystallized from ethyl acetate); yield, 97.4%.

(2) 2',5-dichloro-2-[3-(2-phthalimidoacetamidomethyl)-5-pyrrolidinomethyl-4H-1,2,4-triazol-4-yl]-benzophenone, m.p. about 193° C.; yield, 90.8%.

(3) 2',5-dichloro-2-(3-glycylaminomethyl-5-pyrrolidinomethyl-4H-1,2,4-triazol-4-yl)-benzophenone, m.p. 181°–183° C. (recrystallized from ethanol); Anal. Calcd. for $C_{23}H_{24}N_6Cl_2O_2$: C, 56.68; H, 4.96; N, 17.24; Cl, 14.55. Found: C, 56.66; H, 5.06; N, 17.09; Cl, 14.62; yield, 75%.

EXAMPLE 27

Using 5-chloro-2-(3-carbobenzoxyaminomethyl-5-chloromethyl-4H-1,2,4-triazol-4-yl)-benzophenone and pyrrolidine, the reaction is effected as in Example 22, whereby the following products are obtained:

(1) 5-chloro-2-(3-carbobenzoxyaminomethyl-5-pyrrolidinomethyl-4H-1,2,4-triazol-4-yl)-benzophenone, m.p. 174.5°–175.5° C. (recrystallized from methylene chloride/95% ethanol); yield, 92.1%.

(2) 5-chloro-2-[3-(2-phthalimidoacetamidomethyl)-5-pyrrolidinomethyl-4H-1,2,4-triazol-4-yl]-benzophenone, m.p. 245°–247° C. (decomp.)(recrystallized from methylene chloride/95% ethanol); yield, 68.7%.

(3) 5-chloro-2-(3-glycylaminomethyl-5-pyrrolidinomethyl-4H-1,2,4-triazol-4-yl)-benzophenone, m.p. 182°–183° C. (recrystallized from isopropanol); Anal. Calcd. for $C_{23}H_{25}O_2N_6Cl$: C, 60.99; H, 5.56; N, 18.56; Cl, 7.83. Found: C, 61.08; H, 5.61; N, 18.56; Cl, 8.13; yield, 72.3%.

EXAMPLE 28

(1) To a solution of sodium iodide (1.51 g) in acetonitrile (30 ml), 5-chloro-2-(3-carbobenzoxyaminomethyl-5-chloromethyl-4H-1,2,4-triazol-4-yl)-benzophenone (5.0 g) is added, and the resultant mixture is stirred at room temperature for 18 hours. The reaction mixture is poured into water (100 ml) and shaken with benzene (50 ml) twice. The benzene layer is washed with water (100 ml) twice, dried over magnesium sulfate and evaporated under reduced pressure to remove the benzene. The residue is chromatographed on a column of silica gel, which is eluted with ethyl acetate to give 5-chloro-2-(3-carbobenzoxyaminomethyl-5-iodomethyl-4H-1,2,4-triazol-4-yl)-benzophenone (3.61 g). The product is recrystallized from methylene chloride/ether to give crystals melting at 133° to 134° C. (decomp.).

(2) To a solution of thallous ethoxide (1.53 g) in dry benzene (60 ml), propargyl alcohol (0.354 ml) is added, and the resultant mixture is stirred at room temperature for 1 hour. The mixture is evaporated under reduced pressure to give thallium propargyloxide in a form of white crystals, which is dissolved in dry acetonitrile (60 ml). The above product (3.00 g) is added to the solution, which is stirred at room temperature for 42 hours. The precipitate is filtered off, and the filtrate is evaporated under reduced pressure to remove the solvent. The residue is dissolved in benzene (50 ml), washed with water thrice, dried over magnesium sulfate and evaporated under reduced pressure to remove the benzene. The residue is chromatographed on a column of silica gel, which is eluted with 10 to 50% ethyl acetate/methylene chloride to give 5-chloro-2-(3-carbobenzoxyaminomethyl-5-propargyloxymethyl-4H-1,2,4-triazol-4-yl)-benzophenone (817 mg) as an oil.

(3) A mixture of the above product (817 mg) and 27.5% hydrogen bromide/acetic acid (3 ml) is stirred at room temperature for 1.5 hours. The resultant solution is mixed with dry ether (30 ml) to give a precipitate. The precipitate is washed with dry ether (20 ml) twice to give 5-chloro-2-(3-aminomethyl-5-propargyloxymethyl-4H-1,2,4-triazol-4-yl)-benzophenone hydrobromide. To a suspension of this hydrobromide in dry benzene (20 ml), 2-phthalimidoacetyl chloride (1.6 g) is added at room temperature. The resultant mixture is mixed with dry dimethylformamide (10 ml) and stirred at room temperature for 3 hours. The reaction mixture is poured into saturated aqueous sodium bicarbonate (50 ml)/water (50 ml) and stirred under ice-cooling for 30 minutes. The precipitate is filtered, washed with water and ether in order and dissolved in methylene chloride (about 50 ml). The organic layer is dried over magnesium sulfate and evaporated to remove the solvent. The residue is recrystallized from methylene chloride/ethanol to give 5-chloro-2-[3-(2-phthalimidoacetamidomethyl)-5-propargyloxymethyl-4H-1,2,4-triazol-4-yl]-benzophenone (682 mg) as crystals melting at 245° to 246° C. (decomp.). (4) A solution of the above product (600 mg) and hydrazine hydrate (1.0 ml) in 95% ethanol (10 ml) is refluxed for 2 hours. The precipitate is filtered off, and the filtrate is evaporated under reduced pressure to remove the solvent. The residue is extracted with methylene chloride, and the methylene chloride layer is shaken with 2N hydrochloric acid (50 ml) twice. The hydrochloric acid layer is made alkaline with aqueous ammonia and shaken with methylene chloride thrice. The methylene chloride layer is dried over potassium carbonate to give 5-chloro-2-(3-glycylaminomethyl-5-propargyloxymethyl-4H-1,2,4-triazol-4-yl)-benzophenone hydrate as a colorless oil. The product is crystallized from isopropanol/ether to give crystals melting at 93° to 95° C.

Anal. Calcd. for $C_{22}H_{20}O_3N_5Cl.H_2O$: C, 57.96; H, 4.87; N, 15.36; Cl, 7.78. Found: C, 58.32; H, 4.88; N, 15.44; Cl, 8.15.

EXAMPLE 29

Using 5-chloro-2'-fluoro-2-(3-carbobenzoxyaminomethyl-5-chloromethyl-4H-1,2,4-triazol-4-yl)-benzophenone (m.p. 148°–149° C.) and morpholine, the reaction is effected as in Example 22, whereby the following products are obtained:

(1) 5-chloro-2'-fluoro-2-(3-carbobenzoxyaminomethyl-5-morpholinomethyl-4H-1,2,4-triazol-4-yl)-benzophenone, m.p. 182°–184.5° C. (recrystallized from ethyl acetate).

(2) 5-chloro-2'-fluoro-2-[3-(2-phthalimidoacetamidomethyl)-5-morpholinomethyl-4H-1,2,4-triazol-4-yl]-benzophenone, m.p. 269°–270° C. (recrystallized from methylene chloride/methanol).

(3) 5-chloro-2'-fluoro-2-(3-glycylaminomethyl-5-morpholinomethyl-4H-1,2,4-triazol-4-yl)-benzophenone, amorphous form.

EXAMPLE 30

(1) A solution of 2',5-dichloro-2-(3-glycylaminomethyl-5-methyl-4H-1,2,4-triazol-4-yl)-benzophenone (1.18 g), phthalylglycine (100 g) and dicyclohexylcarbodiimide (1.05 g) in dimethylformamide (23 ml) is stirred at room temperature for 3 hours, and the reaction mixture is allowed stand overnight. The precipitated urea is filtered off. The filtrate is mixed with excess of aqueous sodium carbonate, and the precipitate is separated by decantation. The residue is dissolved in methylene chloride, washed with water, dried and concentrated. Crude product is columned on silica gel (ethyl acetate:methanol = 1:4), and recrystallized from chloroform-methanol to give 2',5-dichloro-2-[3-($N^\alpha$-2-phthalimidoacetylglycylaminomethyl)-5-methyl-4H-1,2,4-triazol-4-yl]-benzophenone (1.35 g) as crystals melting at 269° to 270° C.

(2) A suspension of the above product (1.10 g) and hydrazine hydrate (0.25 ml) in ethanol (10 ml) is stirred at reflux temperature for 2.5 hours. The reaction mixture is allowed to cool to room temperature, and the precipitated phthalylhydrazide is filtered off. The filtrate is concentrated under reduced pressure, and the residue is extracted with ethyl acetate. The ethyl acetate layer is washed with aqueous sodium bicarbonate, dried, and evaporated under reduced pressure to remove the solvent. The residue is recrystallized from acetate/n-hexane to give 2',5-dichloro-2-[3-($N^\alpha$-glycyl-glycylaminomethyl)-5-methyl-4H-1,2,4-triazol-4-yl]-benzophenone (210 mg) as hygroscopic crystals melting at 60° to 65° C.

EXAMPLE 31

(1) A solution of 2',5-dichloro-2-(3-glycylaminomethyl-5-methyl-4H-1,2,4-triazol-4-yl)-benzophenone (1.08 g) and phthalyl-L-phenylalanine (800 mg) in dimethylformamide (13 ml) is mixed with a solution of dicyclohexylcarbodiimide (450 mg) in dimethylformamide (3 ml) at room temperature. The resultant mixture is stirred at room temperature for 4 hours and allowed to stand overnight. The reaction mixture is treated as in Example 30 (1), whereby 2',5-dichloro-2-{3-[$N^\alpha$-(L-2-benzyl-2-phthalimidoacetyl)-glycylaminomethyl]-5-methyl-4H-1,2,4-triazol-4-yl}-benzophenone (1.12 g) is obtained as crystals melting at 138° to 140° C. (recrystallized from methylene chloride/n-hexane).

(2) The above product is treated with hydrazine hydrate as in Example 30 (2), whereby 2',5-dichloro-2-[3-($N^\alpha$-L-phenylalanyl-glycylaminomethyl)-5-methyl-4H-1,2,4-triazol-4-yl]-benzophenone is obtained as hygroscopic crystals melting at 65° to 70° C.

The dihydrochloride hydrate: m.p. 187°–190° C. (recrystallized from ethanol-ether).

EXAMPLE 32

(1) A suspension of 5-chloro-2-(3-carbobenzoxyaminomethyl-5-chloromethyl-4H-1,2,4-triazol-4-yl)-benzophenone (1.0 g) and silver acetate (0.5 g) in acetonitrile (20 ml) is refluxed for 2 hours. The precipitated silver chloride is filtered off, and the filtrate is evaporated under reduced pressure. The residue is dissolved in ethyl acetate. The ethyl acetate solution is washed with water, dried, and evaporated under reduced pressure to give a pale yellow oil. The residue is chromatographed on a column of silica gel, which is eluted with ethyl acetate to give 5-chloro-2-(3-carbobenzoxyaminomethyl-5-acetoxymethyl-4H-1,2,4-triazol-4-yl)-benzophenone (0.65 g) as a colorless oil.

IR (film), 3280 (broad), 1745, 1715, 1660, 1595 cm$^{-1}$.

(2) A mixture of the above product (650 mg) and 30% hydrogen bromide/acetic acid (2 ml) is stirred at room temperature for 1 hour. The resultant mixture is mixed with excess of ether, and the precipitate is washed with ether thrice by decantation to give 5-chloro-2-(3-aminomethyl-5-acetoxymethyl-4H-1,2,4-triazol-4-yl)-benzophenone hydrobromide. To a suspension of the above product and 2-phthalimidoacetyl chloride (1.0 g) in benzene (10 ml), dimethylformamide (5 ml) is added at room temperature, and the resultant mixture is stirred for 3 hours. The reaction mixture is mixed with aqueous saturated sodium bicarbonate and extracted with methylene chloride. The ethyl acetate layer is washed thoroughly with water, dried over anhydrous sodium sulfate, and evaporated under reduced pressure to remove the solvent. The residual oil is triturated with ethyl acetate to give crystalline 5-chloro-2-[3-(2-phthalimidoacetamidomethyl)-5-acetoxymethyl-4H-1,2,4-triazol-4-yl]-benzophenone (700 mg). The product is recrystallized from ethanol to give crystals melting at 225° to 228° C.

(3) A suspension of the above product (522 mg) and 100% hydrazine hydrate (45 mg) in ethanol (20 ml) is refluxed for 2 hours. The resultant mixture is evaporated under reduced pressure, and the residue is partitioned between methylene chloride and aqueous saturated sodium carbonate. The methylene chloride layer is separated, dried over anhydrous sodium sulfate, and evaporated to remove the solvent. The residue is chromatographed on a column of silica gel, which is eluted with ethyl acetate-methanol (v/v = 4/1) to give 5-chloro-2-(3-glycylaminomethyl-5-acetoxymethyl-4H-1,2,4-triazol-4-yl)-benzophenone.½$H_2O$ (120 mg). The product is recrystallized from ethyl acetate to give crystals melting at 123° C. (contracted).

IR (Nujol), 3220, 1745, 1655 (broad), 1590 cm$^{-1}$.

Anal. Calcd. for $C_{21}H_{20}N_5Cl.\frac{1}{2}H_2O$: C, 55.94; H, 4.69; N, 15.53. Found: C, 55.76; H, 4.52; N, 15.71.

EXAMPLE 33

(1) To a solution of L-2-phthalimido-3-phenylpropionyl chloride (2.7 g) in benzene (26ml) and dimethylformamide (13 ml), 2',5-dichloro-2-(3-aminomethyl-5-methyl-4H-1,2,4-triazol-4-yl)-benzophenone dihydrobromide (3 g) is added at 0° C. in an ice bath with stirring. The reaction mixture is gradually warmed to room temperature and left on standing overnight. Aqueous saturated sodium bicarbonate is poured into the mixture, and the benzene layer is separated, dried over anhydrous sodium sulfate and evaporated under reduced pressure to remove the solvent, whereby 2',5-dichloro-2-[3-(L-2-benzyl-2-phthalimidoacetamidomethyl)-5-methyl-4H-1,2,4-triazol-4-yl]-benzophenone (2.5 g) is obtained as crystals melting at 238° to 240° C. IR (Nujol), 3190, 1780, 1715, 1680 (broad), 1590 cm$^{-1}$.

(2) A suspension of the above product (2.4 g) and 100% hydrazine hydrate (0.2 g) in ethanol (20 ml) is refluxed for 1 hour. The precipitate is filtered off, and filtrate is evaporated under reduced pressure. The residue is partitioned between methylene chloride and aqueous saturated sodium bicarbonate. The methylene chloride layer is dried over anhydrous sodium sulfate and evaporated. The viscous oil is treated with oxalic acid (400 mg) in ethyl acetate (15 ml) to give white precipitates. The precipitates are washed with ethyl acetate several times to give 2',5-dichloro-2-(3-L-phenylalanylaminomethyl-5-methyl-4H-1,2,4-triazol-4-yl)-benzophenone oxalate hydrate (1.9g).

Anal. Calcd. for $C_{28}H_{27}N_5O_7Cl_2$: C, 54.55, H, 4.41; N, 11.36; Cl, 11.50. Found: C, 54.13; H, 4.34; N, 11.06; Cl, 11.31.

$[\alpha]_D + 29°$ (EtOH).

EXAMPLE 34-37.

Using acyl chloride (X), the reaction is effected as in Example 33 (1), whereby the corresponding products (Ie) are obtained:

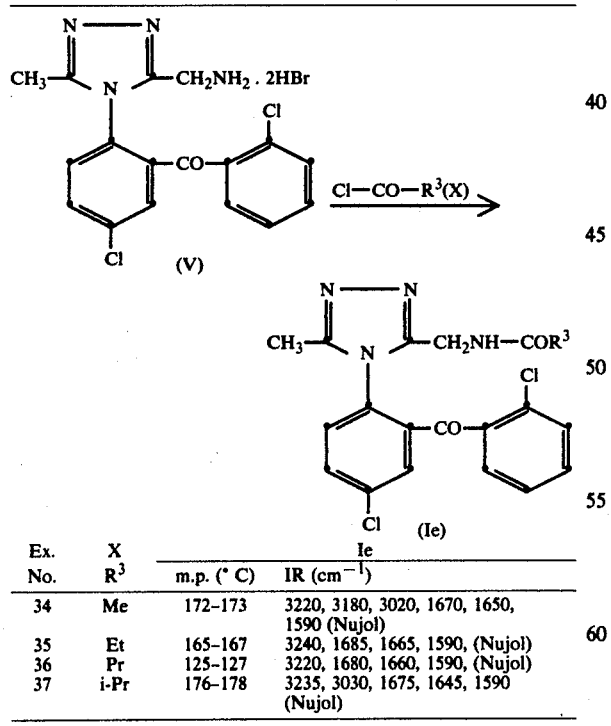

| Ex. No. | X R$^3$ | Ie m.p. (° C) | IR (cm$^{-1}$) |
|---|---|---|---|
| 34 | Me | 172–173 | 3220, 3180, 3020, 1670, 1650, 1590 (Nujol) |
| 35 | Et | 165–167 | 3240, 1685, 1665, 1590, (Nujol) |
| 36 | Pr | 125–127 | 3220, 1680, 1660, 1590, (Nujol) |
| 37 | i-Pr | 176–178 | 3235, 3030, 1675, 1645, 1590 (Nujol) |

EXAMPLE 38

Using 5-chloro-2-(3-carbobenzoxyaminomethyl-5-chloromethyl-4H-1,2,4-triazol-4-yl)-benzophenone and dimethylamine, the reaction is effected as in Example 22, whereby the following products are obtained.

(1) 5-chloro-2-(3-carbobenzoxyaminomethyl-5-dimethylaminomethyl-4H-1,2,4-triazol-4-yl)-benzophenone, m.p. 123°–125° C.; IR (CHCl$_3$), 3210, 1708, 1655 cm$^{-1}$.

(2) 5-chloro-2-[3-(2-phthalimidoacetamidomethyl)-5-dimethylaminomethyl-4H-1,2,4-triazol-4-yl]-benzophenone, m.p. 229°–231° C. (recrystallized from ethanol); IR (Nujol), 3200, 1770, 1715, 1680, 1658 cm$^{-1}$.

(3) 5-chloro-2-(3-glycylaminomethyl-5-dimethylaminomethyl-4H-1,2,4-triazol-4-yl)-benzophenone, m.p. 188°–190° C; IR (Nujol), 3340, 3200, 1680 cm$^{-1}$.

Anal. Calcd. for $C_{21}H_{23}N_6O_2Cl$: C, 59.08; H, 5.48; N, 19.69; Cl, 8.30. Found: C, 59.21; H, 5.25; N, 19.56; Cl, 8.43.

EXAMPLE 39

Using 5-chloro-2-(3-carbobenzoxyaminomethyl-5-chloromethyl-4H-1,2,4-triazol-4-yl)-benzophenone and piperidine, the reaction is effected as in Example 22, whereby the following products are obtained.

(1) 5-chloro-2-(3-carbobenzoxyaminomethyl-5-piperidinomethyl-4H-1,2,4-triazol-4-yl)-benzophenone, m.p. 169°–171° C. (recrystallized from ethyl acetate); IR (Nujol), 3180, 1705, 1670 cm$^{-1}$.

(2) 5-chloro-2-[3-phthalimidoacetamidomethyl-5-piperidinomethyl-4H-1,2,4-triazol-4-yl]-benzophenone, m.p. 246°–248° C. (recrystallized from ethanol); IR (Nujol), 3220, 1765, 1715, 1695, 1660 cm$^{-1}$.

(3) 5-chloro-2-(3-glycylaminomethyl-5-piperidinomethyl-4H-1,2,4-triazol-4-yl)-benzophenone,$\frac{1}{2}C_2H_5OCOCH_3$, m.p. 288° C.; IR (Nujol), 3220, 1730, 1680, 1660, 1590 cm$^{-1}$.

Anal. Calcd. for $C_{26}H_{31}N_6O_3Cl$: C, 61.11, H, 6.11; N, 16.44; Cl, 6.94. Found: C, 60.88; H, 6.23; N, 16.30; Cl, 7.14.

EXAMPLE 40

Using 5-chloro-2-(3-carbobenzoxyaminomethyl-5-chloromethyl-4H-1,2,4-triazol-4-yl)-benzophenone and morpholine, the reaction is effected as in Example 22, whereby the following products are obtained.

(1) 5-chloro-2-(3-carbobenzoxyaminomethyl-5-morpholinomethyl-4H-1,2,4-triazol-4-yl)-benzophenone, m.p. 175°–176° C. (recrystallized from ethyl acetate); IR (Nujol), 3220, 1710, 1670 cm$^{-1}$.

(2) 5-chloro-2-[3-(2-phthalimidoacetamidomethyl)-5-morpholinomethyl-4H-1,2,4-triazol-4-yl]-benzophenone, m.p. 248°–250° C. (recrystallized from ethanol); IR (Nujol), 3200, 1765, 1710, 1695, 1660 cm$^{-1}$.

(3) 5-chloro-2-(3-glycylaminomethyl-5-morpholinomethyl-4H-1,2,4-triazol-4-yl)-benzophenone, oil; IR (CHCl$_3$), 3200, 1660 (broad), 1590 cm$^{-1}$; NMR (CDCl$_3$), $\delta$, 2.0–2.9 (4H, m.), 3.1–3.9 (4H, m.), 3.4(2H, s.), 4.37 (2H, ABX), 8.07 (1H, br. m.).

EXAMPLE 41

Using 5-chloro-2-(3-carbobenzoxy-aminomethyl-5-chloromethyl-4H-1,2,4-triazol-4-yl)-benzophenone and dimethylamine, the reaction is effected as in Example 22, whereby the following products are obtained.

(1) 5-chloro-2-(3-carbobenzoxyaminomethyl-5-dimethylaminomethyl-4H-1,2,4-triazol-4-yl)-benzophenone, m.p. 123°–125° C.

(2) 5-chloro-2-[3-(L-2-benzyl-2-phthalimidoacetamidomethyl)-5-dimethylaminomethyl-4H-1,2,4-triazol-4-yl]-benzophenone, oil; IR (CHCl$_3$), 3300, 3200, 1780, 1715, 1670 cm$^{-1}$.

(3) 5-chloro-2-(3-L-phenylalanylaminomethyl-5-dimethylaminomethyl-4H-1,2,4-triazol-4-yl)-benzophenone, oil; $[\alpha]_D$ −4.0° (EtOH); IR (CHCl$_3$), 3340, 1665 (broad), 1595 cm$^{-1}$, NMR (CDCl$_3$), δ, 1.75 (6H, s.), 2.42 (2H, br. m.), 2.5–3.8 (3H, m.), 4.43 (2H, collapsed ABX), 8.25 (1H, br. m.).

Anal. Calcd. for C$_{28}$H$_{29}$N$_6$O$_2$Cl: C, 65.05; H, 5.65; N, 16.25; Cl, 6.86. Found: C, 64.81; H, 5.56; N, 16.00; Cl, 6.95.

EXAMPLE 42

(1) To a solution of 2′,5-dichloro-2-(3-aminomethyl-5-methyl-2H-1,2,4-triazol-4-yl)-benzophenone dihyrobromide (2.56 g) in dimethylformamide (20 ml), pyridine (0.8 ml) is added under cooling at −10° C., and the resultant mixture is stirred at −10° to −13° C. for 2 minutes. 2-(2-Phthalimidoacetamido)acetyl chloride (4.0 g) is added portionwise thereto, and the mixture is stirred at −10° C. for 3 hours. The reaction mixture is mixed with excess of aqueous sodium bicarbonate, and the precipitated product is separated by filtration and dissolved in methylene chloride (100 ml). The organic layer is washed with water, dried, and evaporated to remove the methylene chloride. The residue is recrystallized from methanol/chloroform to give 2′,5-dichloro-2-[3-(N$^\alpha$-phthalyl-glycyl-glycylaminomethyl)-5-methyl-4H-1,2,4-triazol-4-yl]-benzophenone (2.0 g) as crystals melting at 269° to 270° C.

(2) The above product is hydrazinolyzed as in Example 30 (2), whereby 2′,5-dichloro-2-[3-(N$^\alpha$-glycyl-glycylaminomethyl)-5-methyl-4H-1,2,4-triazol-4-yl]-benzophenone is obtained as crystals melting at 60° to 65° C.

EXAMPLE 43

2′,5-Dichloro-2-(3-glycylaminomethyl-5-dimethylaminomethyl-4H-1,2,4-triazol-4-yl)-benzophenone . . .2.0 g
Wheat starch . . .278.0 g
These are admixed and packed in hard gelatin capsules in a conventional manner, whereby 2,000 capsules are prepared. Each capsule contains 1 mg of 2′,5-dichloro-2-(3-glycylaminomethyl-5-dimethylaminomethyl-4H-1,2,4-triazol-4-yl)-benzophenone as an active ingredient (weight of contents: 140 mg).

What is claimed is:

1. A process for preparing a compound of the formula:

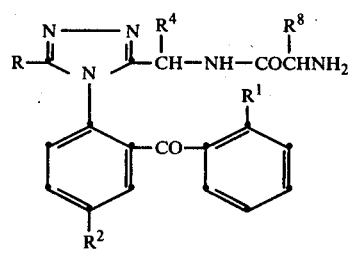

wherein R represents hydrogen, C$_1$–C$_6$ alkyl, C$_1$–C$_6$ chloro-alkyl, C$_1$–C$_6$ bromo-alkyl, C$_1$–C$_6$ fluoro-alkyl, C$_1$–C$_6$ iodo-alkyl, the group —(CH$_2$)$_n$—X—R$^5$, or the group

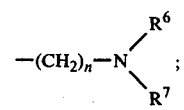

R$^5$ represents hydrogen, C$_1$–C$_6$ alkyl, vinyl, allyl, butenyl, pentenyl, hexenyl, ethynyl, propynyl, butynyl, pentynyl, phenyl, tolyl, xylyl, pyridyl, formyl, acetyl, propionyl, benzoyl, carbobenzoxy, glycyl, alanyl, leucyl or phenylalanyl; X represents sulfur or oxygen; n represents zero, 1, 2, or 3; R$^6$ and R$^7$ each represents hydrogen or C$_1$–C$_6$ alkyl; or the group

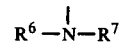

represents pyrrolidino; R$^1$ represents hydrogen or halogen; R$^2$ represents halogen, nitro, or trifluoromethyl; R$^4$ and R$^8$ each represents hydrogen, C$_1$–C$_6$ alkyl, or C$_7$–C$_{10}$ aralkyl, which comprises reducing an azido derivative of the formula:

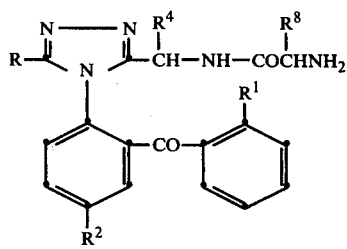

wherein R, R$^1$, R$^2$, R$^4$ and R$^8$ each is as defined above with a reducing agent in an inert solvent, said reducing agent being (1) a mixture containing stannous chloride and sodium hydroxide or (2) zinc dust.